US006912916B1

(12) United States Patent
Joubert

(10) Patent No.: US 6,912,916 B1
(45) Date of Patent: Jul. 5, 2005

(54) POLYVALENT TEST STAND

(75) Inventor: Pierre Joubert, Gentilly (CA)

(73) Assignee: Innovations Industrielles Joubert Inc., Katevale (CA)

( * ) Notice: Subject to any disclaimer, the term of this patent is extended or adjusted under 35 U.S.C. 154(b) by 7 days.

(21) Appl. No.: 10/923,696

(22) Filed: Aug. 24, 2004

(30) Foreign Application Priority Data

Jun. 5, 2004 (CA) .................................. 2470187

(51) Int. Cl.[7] ............................................. G01N 3/02
(52) U.S. Cl. ..................................................... 73/856
(58) Field of Search ......................... 73/760, 855, 856, 73/857, 858, 859, 860

(56) References Cited

U.S. PATENT DOCUMENTS

| | | | | |
|---|---|---|---|---|
| 3,286,515 | A | * | 11/1966 | Bendl ........................... 73/829 |
| 3,879,991 | A | * | 4/1975 | Ristow et al. ................. 73/837 |
| 4,223,554 | A | | 9/1980 | Ulbing |
| 5,216,923 | A | | 6/1993 | Brett |
| 5,677,494 | A | * | 10/1997 | Keener et al. ................. 73/810 |
| 5,948,994 | A | * | 9/1999 | Jen et al. ....................... 73/856 |
| 6,526,837 | B1 | * | 3/2003 | Grote et al. ................... 73/856 |
| 6,629,466 | B2 | * | 10/2003 | Grote et al. ................... 73/857 |

* cited by examiner

*Primary Examiner*—Edward Lefkowitz
*Assistant Examiner*—Takisha Miller

(57) ABSTRACT

A test stand for allowing the testing of both a pull-type lifting apparatus and a push-type lifting apparatus. The test stand includes a base and a carriage component, the carriage component including a load transmitting section and a sensor receiving section. The load transmitting section and the sensor receiving section are spaced apart by spacing members. The spacing members are slidably mounted to the base for allowing a sliding movement of the carriage component relative to the base between a retracted configuration and an extended configuration. A load sensor provides a measurement of a force biasing the carriage component towards the extended configuration. The carriage component is configured and sized for allowing the push-type lifting apparatus to be inserted between the base and the load transmitting section so as to bias the carriage component towards the extended configuration and for allowing the attachment of the pull-type lifting apparatus to the load transmitting section so as to bias the carriage component towards the extended configuration.

42 Claims, 3 Drawing Sheets

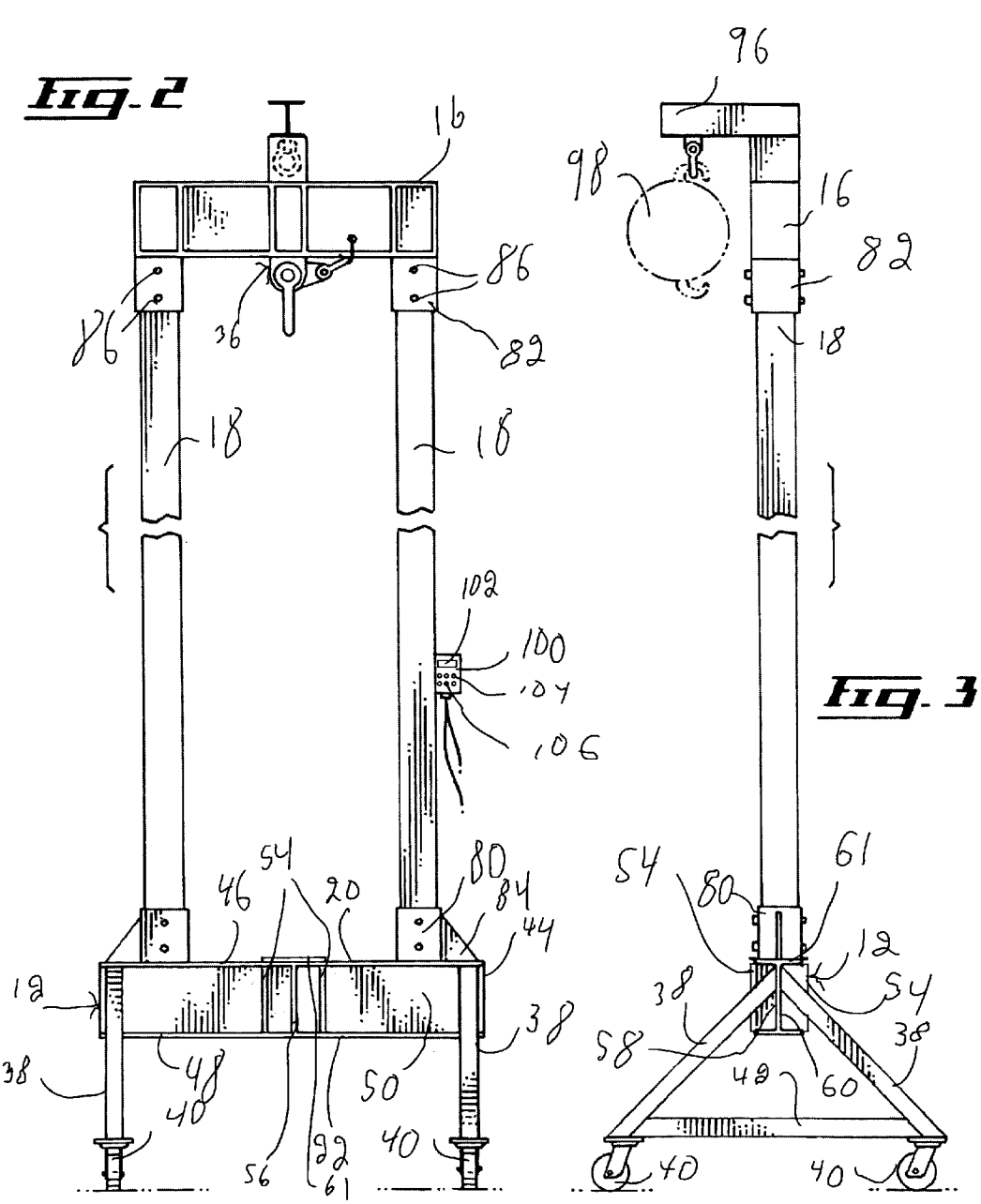

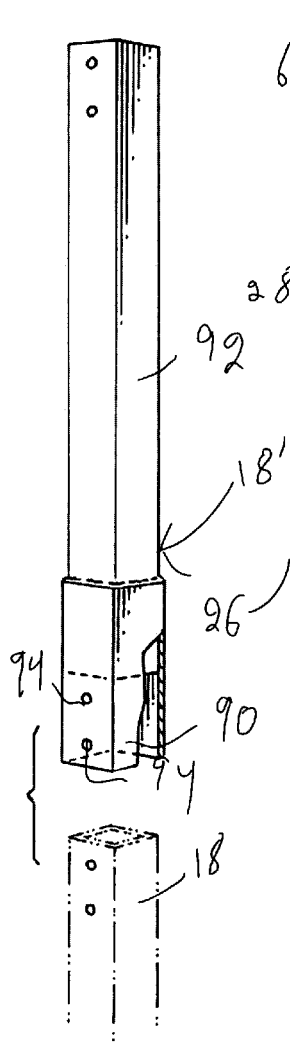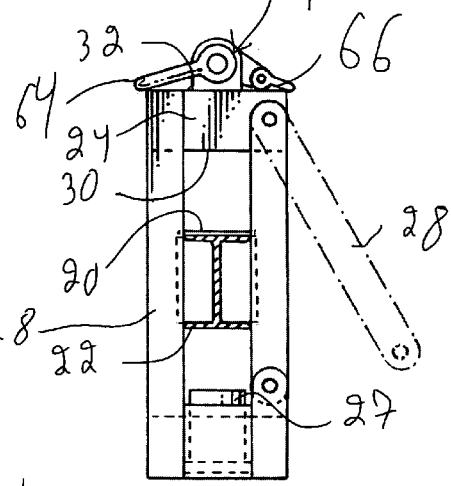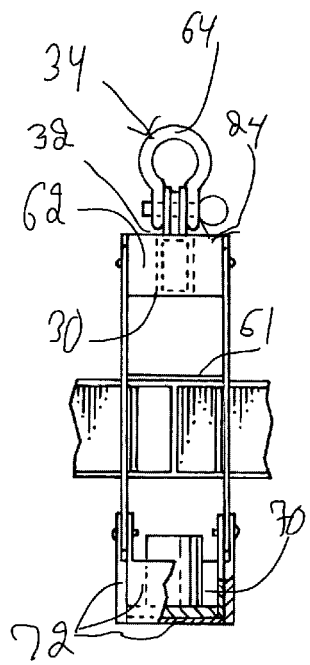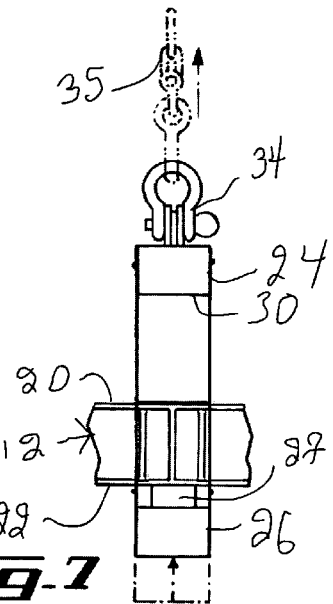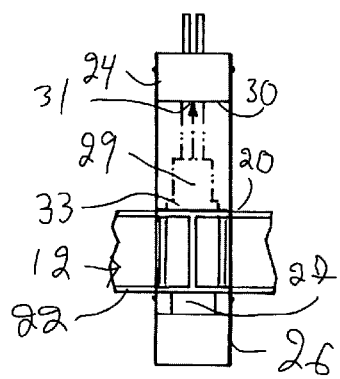

US 6,912,916 B1

POLYVALENT TEST STAND

This application claims priority from Canadian Application Serial Number 2,470,187 filed on Jun. 5, 2004.

FIELD OF THE INVENTION

The present invention relates to test stands. More specifically, the present invention is concerned with a polyvalent test stand for testing a lifting apparatus.

BACKGROUND OF THE INVENTION

Many types of lifting apparatuses, such as hoists, are commonly used in many industries. Such apparatuses allow a user to manipulate relatively heavy loads with relatively little effort.

However, these apparatuses often become damaged, either through normal use or through abuse by their users. In this case, it often happens that the apparatus becomes unsafe and becomes unable to lift a load for which it is normally rated.

By their nature, the loads manipulated by lifting apparatuses are relatively heavy and can cause a lot of damages and injuries if, for any reason, the apparatus breaks and frees the load.

A common type inspection performed within the industry is to remove the apparatus from the place where it is being used and send it to specialized outlets where it is tested. An example of such a test includes loading the apparatus with the load somewhat larger than the rated capacity of the apparatus, and subsequently to examine the apparatus for indications of damage or excessive wear.

For safety reasons, it would be beneficial to perform this type of inspection often. However, since testing requires that the apparatus be removed from its operation site while being tested, users of such apparatuses typically only perform preventive testing at the minimum frequency required by law.

In addition, the removal of the apparatus from its operational site and its shipping to the specialized outlet is relatively expensive, especially in large shops wherein tens, if not hundreds, of apparatuses are used.

U.S. Pat. No. 5,216,923 issued to Brett on Jun. 8, 1993 attempts to solve this problem in the following way. A test stand for industrial slings is built and mounted within a vehicle, in this case a converted school bus. Therefore, the bus can be brought to many sites such that each lifting apparatus is only non-operational for testing for a short amount of time. However, the test stand described in Brett is relatively complex, and because of the vehicle into which it is attached, many small, medium, or even large companies cannot easily acquire it.

In addition, another disadvantage of the apparatus described in Brett is that their testing device is adapted to only test one type of lifting apparatus, namely a sling.

Against this background, there exists a need in the industry to provide a novel polyvalent test stand.

The present description refers to a number of documents, the content of which is herein incorporated by reference in their entirety.

OBJECTS OF THE INVENTION

An object of the present invention is therefore to provide improved polyvalent test stand.

SUMMARY OF THE INVENTION

In a first broad aspect, the invention provides a test stand for allowing the testing of both a pull-type lifting apparatus and a push-type lifting apparatus. The push-type lifting apparatus defines a pair of opposed force transmitting ends. The test stand includes a base defining first and second substantially opposed base surfaces. The test stand further includes a carriage component, the carriage component including a load transmitting section and a sensor receiving section. The load transmitting section and the sensor receiving section are spaced apart by spacing members. The spacing members are slidably mounted to the base for allowing a sliding movement of the carriage component relative to the base between a retracted configuration wherein the load transmitting section is positioned substantially adjacent to the first base surface, and an extended configuration wherein the sensor receiving section is positioned substantially adjacent to the second base surface. A load sensor is located between the second base surface and the sensor receiving section and provides a measurement of a force biasing the carriage component towards the extended configuration. The load transmitting section defines a transmitting section inner surface located substantially opposite the first base surface, and an opposed transmitting section outer surface, the transmitting section outer surface being provided with an attachment allowing the pulling of the load transmitting section so as to allow the pull-type lifting apparatus to bias the carriage component towards the extended configuration. The carriage component is configured and sized for allowing the push-type lifting apparatus to be inserted between the base and the load transmitting section with the opposed force transmitting ends abutting respectively against the first base surface and the transmitting section inner surface, so as to bias the carriage component towards the extended configuration.

Advantageously, the test stand allows for the testing of many types of lifting apparatuses, such as pull-type lifting apparatuses and push-type lifting apparatuses. An example of such a push-type lifting apparatus is a hoist. An example of such a push-type lifting apparatus is a hydraulic or pneumatic jack.

In a variant, the test stand is of a relatively light construction and is mounted on wheels, allowing to relatively easily move the test stand from place to place. Therefore, time and money are saved during testing of the lifting apparatus as the test stand is able to be brought in proximity to the apparatus to test, which reduces a duration for which the apparatus is not available to perform lifting duties.

Also, since testing of lifting apparatuses with the test stand is less time-consuming and expensive than in traditional testing methods, there is an incentive to test lifting apparatuses relatively often, which increases the safety of these lifting apparatuses.

In some variants, the test stand includes a pull-type lifting apparatus receiving section and a connecting member connecting the base and the pull-type lifting apparatus receiving section. The pull-type lifting apparatus receiving section is provided with an attachment allowing attaching the pull-type lifting apparatus between the pull-type lifting apparatus receiving section and the transmitting section outer surface. In some embodiments of the invention, the connecting member is detachable from the pull-type lifting apparatus receiving section and the base.

Therefore, the test stand in these variants and specific embodiments is relatively easily unassembled and transported from one location to the other. Therefore, it is relatively easy to carry the testing apparatus in proximity to the lifting apparatus, so as to minimize down times during which the apparatus is tested.

In some embodiments of the invention, the test stand is particularly suitable for specialized for businesses that would carry such a stand from location to location and offer testing services. Alternatively, medium to large sized businesses are able to acquire and manipulate their own test stand relatively easily, which saves time and reduces costs, as described hereinabove.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 2 is front elevation view of the test stand of FIG. 1;

FIG. 3 is side elevation view of the test stand of FIG. 1;

FIG. 4 is a perspective view of an alternative embodiment of the connecting member of the test stand of FIG. 1;

FIG. 5 is a side elevation view of the carriage component of the test stand of FIG. 1;

FIG. 6 is a front elevation view of the carriage component of the test stand of FIG. 1;

FIG. 7 illustrates schematically the carriage component of FIG. 5 in an extended configuration and biased by a pull-type lifting apparatus; and FIG. 8 illustrates schematically the carriage component of FIG. 5 in an extended configuration and biased by a push-type lifting apparatus.

DETAILED DESCRIPTION

Figure 1:
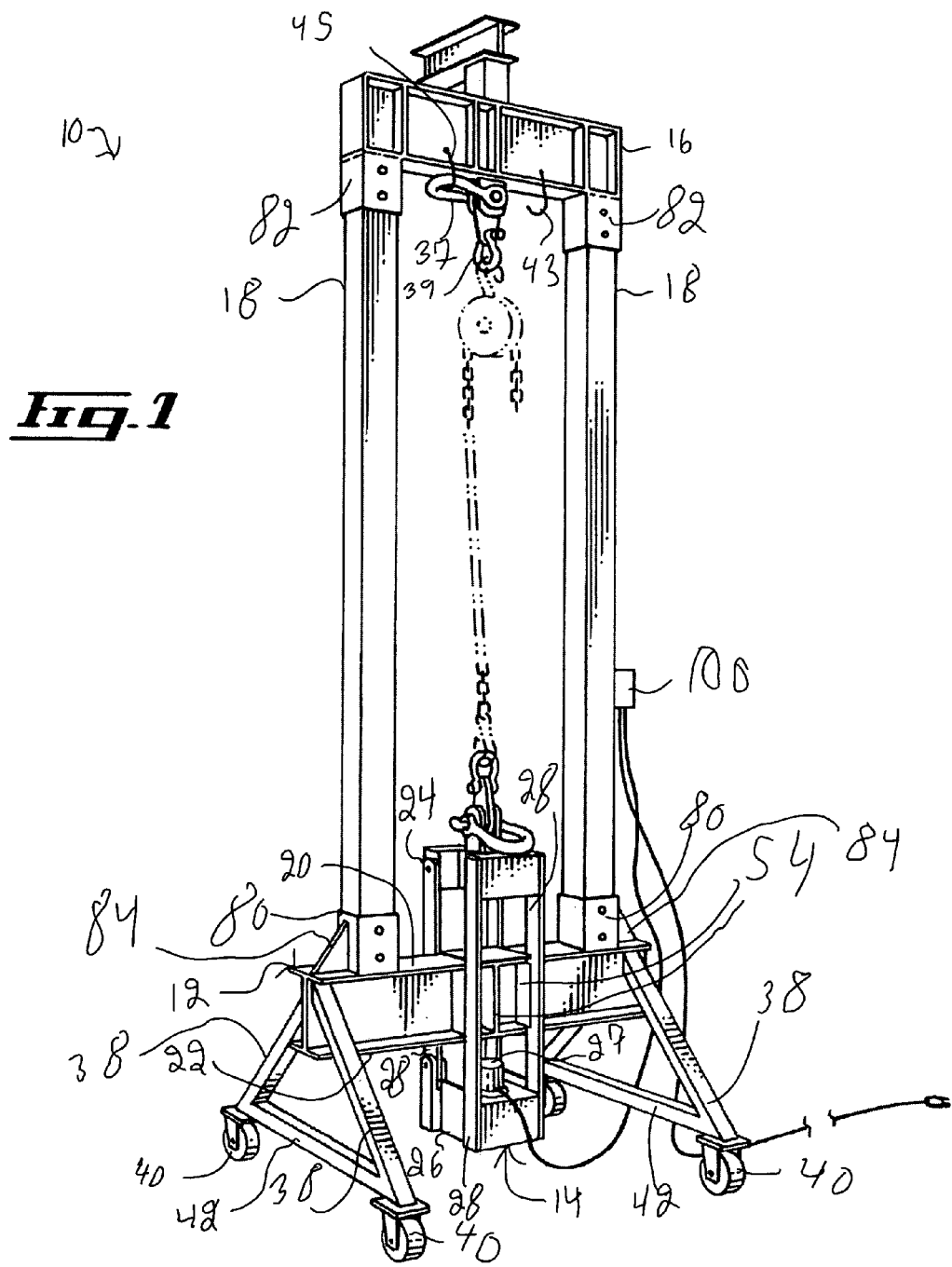
FIG. 1 is perspective view of a test stand including a carriage component and detachable connecting member.

FIG. 1 illustrates a test stand 10 for allowing the testing of both a pull-type lifting apparatus and a push-type lifting apparatus. The test stand 10 includes a base 12 defining two substantially opposed base surfaces 20 and 22, a carriage component 14 slidably mounted to the base 12, a pull-type lifting apparatus receiving section 16 and two connecting members 18 connecting the base 12 and the pull-type lifting apparatus receiving section 16.

The carriage component 14 includes a load transmitting section 24 and a sensor receiving section 26. The load transmitting section 24 and the sensor receiving section 26 are spaced apart by spacing members 28.

The spacing members 28 are slidably mounted to the base 12 and allow a sliding movement of the carriage component 14 relatively to the base 12 between a retracted configuration wherein the load transmitting section is positioned substantially adjacent to the base surface 20 and an extended configuration wherein the sensor receiving section 26 is positioned substantially adjacent to the base surface 22. In the specific embodiment of the invention shown in the drawings, the spacing members 28 are slidably mounted to the base 12 such as to guide the carriage component 14 in a substantially rectilinear movement.

A load sensor 27 is located between the base surface 22 and the sensor receiving section 26 for providing a measurement of a force biasing the carriage component 14 in the extended configuration.

As better shown in FIG. 5, the load transmitting section 24 defines a transmitting section inner surface 30 located substantially opposite the first base surface 20 and an opposed transmitting section outer surface 32, the transmitting section outer surface 32 being provided with an attachment 34 allowing pulling of the load transmitting section 24 so as to allow the pull-type lifting apparatus to bias the carriage component 14 towards the extended configuration.

As illustrated schematically in FIG. 8, the carriage component 14 is configured and sized for allowing the push-type lifting apparatus, which takes the form of a jack 29 in FIG. 8, to be inserted between the base 12 and the load transmitting section 24 with two opposed transmitting ends 33 and 31 of the push-type lifting apparatus abutting respectively against the first base surface 20 and the transmitting section inner surface 30 so as to bias the carriage component 14 towards the extended configuration.

The pull-type lifting apparatus receiving section 16 is provided with an attachment 36 allowing the attachment of the pull-type lifting apparatus between the pull-type lifting apparatus receiving section 16 and the transmitting section outer surface 32. More specifically, the pull-type lifting apparatus attaches also to the attachment 34, as seen in FIG. 7.

In other words, still as shown in FIG. 7, a pull-type lifting apparatus, such as a sling or a hoist 35, is attached between the two attachments 36 and 34 to pull the carriage component 14 such as to bias the carriage component 14 against the second base surface 22. Accordingly, in this case, the load sensor 27 measures a biasing force exerted by the pull-type lifting apparatus.

In addition, the push-type lifting apparatus when inserted between the transmitting section inner surface 30 and the first base surface 20 (see FIG. 8) biases the carriage component 14 as described in the preceding paragraph. Accordingly, also in this case, the load sensor 27 measures a biasing force exerted by the lifting apparatus. Therefore, many types of lifting apparatuses are testable by the test stand 10.

Although the pull-type lifting apparatus receiving section 16 shown in the drawings includes an I-shaped cross-section beam with reinforcing plate, any other suitable pull-type lifting apparatus receiving section 16 is within the scope of the invention.

In addition, if the attachment 36 includes two shackles 37 and 39, as shown in the drawings, it is useful in some embodiments of the invention to provide in the pull-type lifting apparatus receiving section 16 hooks 43 and 45 for attaching respectively the shackles 37 and 39 when they are not in use.

In some embodiments of the invention, as shown in FIGS. 1, 2 and 3, the test stand 10 includes a plurality of legs 38 connected to the base 12. The legs 38 are for supporting the base 12 away from a ground surface onto which the test stand 10 stands. In a specific example shown in the drawings, the test stand includes four legs 38. However, test stands having any suitable number of legs are within the scope of the invention.

Each leg 38 includes a wheel 40 allowing the test stand 10 to be rolled onto the ground surface. In other embodiments of the invention, no wheels 40 are provided.

In some embodiments of the invention, a caster wheel is a particularly suitable type of wheel that is used in conjunction with the test stand 10. However, other types of wheels are also usable without departing from the scope of the invention.

As shown in the drawings, the legs 38 are connected pair-wise by cross members 42. The cross members 42 connecting the legs 38 in proximity to their respective wheels 40. The cross members 42, along with the legs 38, form a triangulated structure that is relatively rigid while keeping a relatively low weight. However, other structures for connecting legs 38, along with the absence of such structures, are also within the scope of the invention.

As better shown in FIG. 2, the base 12 includes a beam 44. The beam 44 is an I-shaped cross-section beam including two parallel base panels 46 and 48 connected through a transverse panel 50. The two base panels 46 and 48 are substantially parallel defining respectively the first and second base surfaces 20 and 22.

In addition, the beam 42 includes flanges 54 extending substantially outwardly from the transverse panel 50. The flanges 54 are also connected to the two panels 46 and 48. The flanges 54 extend further away from the transverse panel 50 than the two base panels 46 and 48.

More specifically, as better seen in FIG. 3, the transverse panel 50 defines two opposed transverse panel surfaces 58 and 60. Two of the flanges 54 extend away from the transverse panel surface 58 and two of the flanges 54 extend away from the transverse panel surface 60.

The flanges 54 guide the spacing members 28 in the rectilinear motion of the carriage component 14. In other words, the flanges 54 act as rails for guiding the movement of the carriage component 14. To that effect, In some embodiments of the invention, additional flanges 56 are also provided similarly to the flanges 54 except that the flanges 56 are mainly present to improve a structural rigidity of the base 20 and do not guide or contact the spacing members 28.

In yet other embodiments of the invention, as shown in the drawings, the base 12 includes a plate 61 on the base surface 20. The plate 61 assists the flanges 54 in guiding the spacing members 28. In alternative embodiments of the invention, the flanges 54 are not present and the plate 61, alone or in combination with another similar plate on the base surface 22, or with any other suitable structure, guide the spacing members 28.

As mentioned hereinabove, the carriage component 14 includes the load transmitting section 24, the sensor receiving section 26 and the spacing members 28. In different embodiments of the invention, the load transmitting section 24, the sensor receiving section 26 and the spacing members 28 take many different forms. A specific example of the forms taken by these parts is described hereinbelow, but the reader skilled in the art will readily appreciate that many other alternative forms are also within the scope of the invention.

As shown in FIGS. 5 and 6, the load transmitting section 24 includes a substantially H-shaped body 62. The body 62 defines the transmitting section inner and outer surfaces 30 and 32 and the attachment 34 is attached thereto. In a specific example of implementation, the attachment 34 includes a shackle 64. In some embodiments of the invention, as shown in the drawings, the attachment 34 includes the shackle 64 and another shackle 66. The shackles 64 and 66 are sized such as to allow the attachment of lifting apparatuses having different lifting capacities.

Indeed, the reader skilled in the art will readily appreciate that lifting apparatuses having a larger lifting capacity are typically larger than lifting apparatuses having a smaller lifting capacity. Accordingly, the shackles 64 and 66 need to be appropriately sized such as to allow a secure attachment of the lifting apparatus to the shackles 64 and 66.

As shown in the drawings, in some embodiments of the invention, the shackles 64 and 66 are detachable from the transmitting section outer surface. Methods and devices for releasably attaching shackles to a body are well known in the art and will therefore not be described in further details.

When the shackles 64 and 66 are detachable, like in the embodiment of the test stand shown in the drawings, they are replaceable by a plate (not shown in the drawings) that attaches to the load receiving section 24. The plate allows testing grabs to ensure that they are still able to grab a plate at their load capacity.

The sensor receiving section 26 includes a cavity 70 receiving at least in part the load sensor 27. An example of a suitable load sensor 27 is a piezoelectric load cell. However, any other suitable load sensor is usable in conjunction with the invention.

The cavity 70 receiving the load sensor is defined by five panels 72 forming a parallelepiped with an open side. The spacing members 28 connect the body 62 to the parallelepiped.

As shown in the drawings, a suitable form for the spacing members 28 is the form of a substantially flat spacing panel. In some embodiments of the invention, the spacing panels are permanently connected to the body and to the parallelepiped, for example, through soldering. In other embodiments of the invention, the spacing panels are pivotably attached to at least one of the body 62 and the parallelepiped and reversibly attached to the other of the body and the parallelepiped. An example of such a manner or reversibly attaching that is, in this case, both pivotal and detachable, is through the use of a nut and a bolt. However, any other suitable attachment is usable in conjunction with the present invention. Among other possibilities, having some spacing panels that are permanently connected and some spacing panels that are at least in part detachable is within the scope of the invention.

In the case wherein two of the spacing panels located on the same side of the base 12 with respect to the transverse panel 50 are such that these two spacing panels are pivotably attached to one of the body 62 and the parallelepiped, for example to the body 62, and reversibly attached to the other of the body 62 and the parallelepiped, for example to the parallelepiped it is then possible to remove the carriage component 14 from the base 12 by detaching these spacing panels from the parallelepiped and having then pivot onto the body 62. This can be seen from FIG. 5.

Such removal is particularly useful when transporting the test stand 10. As mentioned before, the spacing panels are substantially parallel to the flanges 54 and are located, configured and sized such that the flanges 54 guide the carriage component 14 by contacting the spacing panels.

As shown in FIG. 1, in a specific embodiment of the invention, the pull-type lifting apparatus receiving section 16 and the base 12 both define cavities for receiving the connecting members 18. The cavities of the base and of the pull-type lifting apparatus receiving section 16 are defined respectively by tubular members 80 and 82 extending respectively from the base 12 and from the pull-type lifting apparatus receiving section 16.

Although not present in all embodiments of the invention, the tubular members 80 are reinforced by reinforcement plates 84 opposing outwardly directed forces exerted by the connecting members 18 in the test stand 10.

The connecting members 18 take the form of substantially elongated tubular members having a cross-section such that the tubular members are insertable within the cavities defined within the base 12 and the pull-type lifting apparatus receiving section 16. However, in other embodiments of the invention, the connecting members 18 take any other suitable shape.

To secure the connecting members 18 within the cavities, the connecting members 18 each include a pair of bores (not shown in the drawings) extending therethrough and provided in proximity to each end of the connecting member 18. In addition, the tubular members 80 and 82 defining the cavities also include bores substantially aligned with the bores of the connecting members 18, such as to allow the insertion into these bores of bolts 86 (better seen on FIG. 2) allowing, in conjunction with nuts threaded onto the bolts, to secure the connecting members both to the base 12 and to the pull-type lifting apparatus receiving section 16.

The reader skilled in the art will readily appreciate that any other method to secure the connecting members 18 to the pull-type lifting apparatus receiving section 16 and the base 12 are within the scope of the invention, including the use of fasteners other than the bolts 86.

In addition, in some embodiments of the invention, connecting members 18 having different lengths are provided such as to allow to vary a distance between the pull-type apparatus receiving section 16 and the base 12.

In alternative embodiments of the invention, each connecting member 18 used in conjunction with one or more connecting members 18'. As shown in FIG. 4, the connecting members 18' are similar to the connecting members 18 except that the connecting member 18' includes a tubular flange 90 extending substantially outwardly and substantially longitudinally from a body 92. The tubular flange 90 includes bores 94 and is sized to allow the insertion of one of the connecting members 18 into one of the connecting members 18' such as to secure the connecting member 18 to the connecting member 18'. Then, the assembly of the connecting member 18 and the connecting member 18' are attachable to the pull-type lifting apparatus receiving section 16 and the base 12 as described hereinabove with respect to the connecting member 18.

Therefore, the connecting members 18 and 18' provide a modular manner of connecting the base 12 to the pull-type lifting apparatus receiving section 16. This modularity is particularly useful for testing lifting apparatuses having different dimensions. In addition, this modularity allows for the compact transporting of the test stand, as substantially long connecting members 18 need not to be transported.

The body 92 of the connecting member 18' and the connecting member 18 abut such that the force exerted onto the connecting member 18 between the base 12 and the pull-type lifting apparatus receiving section 16 is safely transmitted therebetween. However, in other embodiments of the invention, the body and the connecting members 18 do not contact and forces transmitted between the base 12 and the pull-type lifting apparatus receiving section 16 are transmitted through fasteners attaching the flange 90 and the connecting member 18.

In some embodiments of the invention, the test stand 10 includes a jib 96 for attaching a hoist 98 so as to facilitate a manipulation by an intended user of a pull-type lifting apparatus to attach to the attachment 36 of the pull-type lifting apparatus receiving section 16. In some embodiments of the invention, the jib 96 is detachable from the pull-type lifting apparatus receiving section 16, for example by being attached thereto through bolts and nuts. Alternatively, in other embodiments of the invention, the jib is permanently connected to the pull-type lifting apparatus receiving section 16, such as, for example, through soldering.

The test stand 10 further includes a display unit 100 connected to the load sensor 27 for indicating a value of a force measured by the load sensor 27. As shown in FIG. 2, the display unit includes a numerical display 102 for displaying a magnitude of force measured by the load sensor. Also, the display unit includes indicators activated when the force measured by the load sensor reaches a predetermined magnitude. The predetermined magnitude for a specific test is determined by any suitable means, for example through the use of push-buttons 106 located in proximity to the indicators.

The indicator in the specific embodiment shown in the drawings takes the form of light bulbs 104. However, any other suitable indicator is usable in conjunction with the invention. In addition to visual indicators, as light bulbs, sound-producing indicators, such as speakers, are within the scope of the invention.

In use, the test stand is first assembled by mounting the carriage component 14 to the base 12, and by inserting the connecting members 18 within the cavities of the base 12 as well as by inserting the connecting members 18 into the cavities of the pull-type lifting apparatus receiving section 16.

Then, a lifting apparatus to test is suitably either attached to the attachments 34 and 36, in the case of the pull-type lifting apparatus, or inserted between the surfaces 20 and 22. Then, the lifting apparatus is operated according to its normal operating mode.

In other words, if the lifting apparatus is a manual lifting apparatus, a user manipulates the apparatus such as to move the carriage component 14 towards the extended configuration. In the case wherein the lifting apparatus is a hydraulic, pneumatic or electric lifting apparatus, an operator operates the lifting apparatus using a suitable hydraulic, pneumatic or electric system.

In a specific example of implementation, the operator operates the lifting apparatus until a load measured by the load sensor 27 reaches a predetermined load. For example, such a predetermined load is a load twice as large as the rated load capacity of the lifting apparatus.

To that effect, the operator examines the numerical display of the display unit and operates the lifting apparatus until the predetermined load is achieved or alternatively, the operator operates the lifting apparatus until a specific indicator on the display unit is activated.

Then, if the lifting apparatus is still intact further to the previous steps, the lifting apparatus is classified as being still operational. Also, while the lifting apparatus exerts the biasing force, the operator might perform any suitable tests, such as visual inspection, among others, to determine if the lifting apparatus is damaged or worn beyond normal wear.

In some cases, for example in testing of chains, a length measuring device is attached to the lifting apparatus such as to measure an elongation of the lifting apparatus under load. The length measuring device in some embodiments of the invention connected to the display unit 100, which then displays and optionally records the measured elongations.

The test stand 10 is periodically calibrated ensure the load sensor 27 provides accurate measurements. Methods and devices for calibrating test stands and the intervals at which they must be performed are well-known in the art and will therefore not be described in further details.

In alternative embodiments of the invention, the pull-type lifting apparatus receiving section 16 and the connecting members 18 are not provided and are instead replaced by a suitable structure fixed within a room of a building into which the test stand is operated. In this case, in some embodiments of the invention, attachments for maintaining the legs 38 in proximity to the ground are provided. Such attachments are well known in the art and will therefore not be described in further detail.

In other embodiments of the invention, the connecting members 18 are not detachable from the base 12 or from the pull-type lifting apparatus receiving section. Instead, the connecting members 18 permanently connect, for example through soldering, the pull-type lifting apparatus receiving section 16 and the base 12.

In alternative embodiments of the invention, the load sensor 27 is covered with and securely connected a lid that slides within the parallepiped of the sensor-receiving section 26.

Although the present invention has been described hereinabove by way of preferred embodiments thereof, it can be modified, without departing from the spirit and nature of the subject invention as defined in the appended claim.

What is claimed is:

1. A test stand for allowing testing of both a pull-type lifting apparatus and a push-type lifting apparatus, the push-type lifting apparatus defining a pair of opposed force transmitting ends, said test stand comprising:
   a. a base defining first and second substantially opposed base surfaces;
   b. a carriage component including:
      i. a load transmitting section;
      ii. a sensor receiving section;
      iii. said load transmitting section and said sensor receiving section being spaced apart by spacing members, said spacing members being slidably mounted to said base for allowing a sliding movement of said carriage component relatively to said base between a retracted configuration wherein said load transmitting section is positioned substantially adjacent to said first base surface and an extended configuration wherein said sensor receiving section is positioned substantially adjacent to said second base surface; and
      iv. a load sensor located between said second base surface and said sensor receiving section for providing a measurement of a force biasing said carriage component in said extended configuration;
   c. said load transmitting section defining a transmitting section inner surface located substantially opposite said first base surface and an opposed transmitting section outer surface, said transmitting section outer surface being provided with an attachment allowing to pull said load transmitting section so as to allow the pull-type lifting apparatus to bias said carriage component towards extended configuration;
   d. said carriage component being configured and sized for allowing said push-type lifting apparatus to be inserted between said base and said load transmitting section with the opposed force transmitting ends abutting respectively against said first base surface and said transmitting section inner surface so as to bias said carriage component towards said extended configuration.

2. A test stand as defined in claim 1 wherein said spacing members are slidably mounted to said base such as to guide said carriage component in a substantially rectilinear movement.

3. A test stand as defined in claim 2, wherein said test stand is supportable by a ground surface, said test stand further comprising a plurality of legs connected to said base for supporting said base away from the ground surface.

4. A test stand as defined in claim 3, wherein said legs each include a wheel allowing said stand to be rolled onto the ground surface.

5. A test stand as defined claim 4, wherein at least one of said wheels is a caster wheel.

6. A test stand as defined in claim 4 wherein a first leg from said plurality of legs and a second leg from said plurality of legs are connected through a cross-member, said cross-member being connected to said first and second legs in proximity to their respective wheels.

7. A test stand as defined in claim 2, wherein said base includes a beam, said beam including first and second substantially parallel base panels connected through a transverse panel, said transverse panel being substantially perpendicular to said first and second base panels, said first and second base panels defining respectively said first and second base surfaces.

8. A test stand as defined in claim 7, wherein said beam includes a flange extending substantially outwardly from said transverse panel.

9. A test stand as defined in claim 8, wherein said flange is connected to said first and second base panels.

10. A test stand as defined in claim 8, wherein said flange extends further away from said transverse panel than said first and second base panels.

11. A test stand as defined in claim 10, wherein said flange is for guiding at least one of said spacing members.

12. A test stand as defined in claim 10, wherein said flange does not contact any of said spacing member.

13. A test stand as defined in claim 11, wherein:
   a. said transverse panel defines first and second opposed transverse panel surfaces;
   b. said test stand comprises four flanges extending away from said transverse panel further than said first and second base panels, each of said four flanges being in proximity to a respective spacing member from said spacing members, two of said four flanges extending from said first transverse panel surface and two of said four flanges extending from said second transverse panel surface.

14. A test stand as defined in claim 8, wherein said load transmitting section includes a substantially H-shaped body.

15. A test stand as defined in claim 14, wherein said sensor receiving section includes a cavity receiving at least in part said load sensor.

16. A test stand as defined in claim 15, wherein said cavity is defined by five panels forming a parallelepiped with an open side.

17. A test stand as defined in claim 16 wherein said spacing members include at least four spacing members, each spacing member from said at least four spacing members connecting said body to said parallelepiped.

18. A test stand as defined in claim 17, wherein at least one of said at least four spacing members includes a substantially flat spacing panel.

19. A test stand as defined in claim 18, wherein said spacing panel is permanently connected to said body and to said parallelepiped.

20. A test stand as defined in claim 18, wherein said spacing panel is pivotably attached to at least one of said body and said parallelepiped.

21. A test stand as defined in claim 20, wherein said spacing panel is reversibly attached to at least one of said body and said parallelepiped.

22. A test stand as defined in claim 21, wherein said spacing panel is attached to at least one of said body and said parallelepiped through a nut and a bolt.

23. A test stand as defined in claim 18, wherein said spacing panel is substantially parallel to said flange and located, configured and sized such that said flange guides said carriage component by contacting said spacing panel.

24. A test stand as defined in claim 2, wherein said attachment is detachable from said transmitting section outer surface.

25. A test stand as defined in claim 24, wherein said attachment includes a shackle.

26. A test stand as defined in claim 2, wherein said sensor includes a piezoelectric load cell.

27. A test stand as defined in claim 2, further comprising a pull-type lifting apparatus receiving section and a connecting member connecting said base and said pull-type lifting apparatus receiving section, said pull-type lifting apparatus receiving section being provided with an attachment allowing to attach the pull-type lifting apparatus between said pull-type lifting apparatus receiving section and said transmitting section outer surface.

28. A test stand as defined in claim 27, wherein said pull-type lifting apparatus receiving section defines a cavity for receiving said connecting member.

29. A test stand as defined in claim 28, wherein said base defines a cavity for receiving said connecting member.

30. A test stand as defined in claim 29, wherein said cavity of said base and said cavity of said pull-type lifting apparatus receiving section are defined respectively by a first and a second tubular member extending respectively from said base and said pull-type lifting apparatus receiving section.

31. A test stand as defined in claim 30, wherein said connecting member includes a first bore extending therethrough and said first tubular member includes a second and a third bore aligned with said first bore to allow the insertion through said first, second and third bores of a fastener for locking said connecting member within said first cavity.

32. A test stand as defined in claim 30, wherein said connecting member includes a first bore extending therethrough and said second tubular member includes a second and a third bore aligned with said first bore to allow the insertion through said first, second and third bores of a fastener for locking said connecting member within said second cavity.

33. A test stand as defined in claim 27, wherein:
a. said connecting member is a first connecting member, said first connecting member being substantially elongated and defining a longitudinal axis, said first connecting member including a body and a tubular flange extending substantially outwardly and substantially longitudinally therefrom;
b. said test stand further comprises a second substantially elongated connecting member defining a longitudinal axis, said second connecting member including a body and a tubular flange extending substantially outwardly and substantially longitudinally therefrom;
c. said flange of said first connecting member and said body of said second connecting member being configured and sized such that said flange of said first connecting member received said body of said second connecting member.

34. A test stand as defined in claim 33, wherein:
a. said flange of said first connecting member includes a first and a second bore extending therethrough; and
b. said body of said second connecting member includes a third bore extending therethrough;
c. said first, second and a third bores being aligned such as to allow the insertion through said first, second and third bores of a fastener for locking said connecting member within said second cavity.

35. A test stand as defined in claim 34, wherein said fastener includes a nut and a bolt.

36. A test stand as defined in claim 33, wherein said body of said first connecting member abuts said body of said second connecting member.

37. A test stand as defined in claim 36, wherein said attachment of said pull-type lifting apparatus receiving section includes a shackle.

38. A test stand as defined in claim 27, wherein said pull-type lifting apparatus receiving section includes a jib for attaching a hoist such as to facilitate a manipulation by an intended user of pull-type lifting apparatus to attach to said attachment of said pull-type lifting apparatus receiving section.

39. A test stand as defined in claim 38, wherein said jib is detachable from said pull-type lifting apparatus receiving section.

40. A test stand as defined in claim 2, further comprising a display unit connected to said load sensor for indicating a value of a force measured by said load sensor.

41. A test stand as defined in claim 40, wherein said display unit includes a numerical display for displaying the magnitude of the force measured by said load sensor.

42. A test stand as defined in claim 40, wherein said display unit includes an indicator, said indicator being activated when the force measured by said load sensor reaches a predetermined magnitude.

* * * * *